(12) United States Patent
Tanaka (10) Patent No.: US 9,603,755 B2
(45) Date of Patent: Mar. 28, 2017

(54) ABSORBENT ARTICLE WITH KLEMM GRADIENT AND WATER REPELLENT FINISHING

(71) Applicant: KAO CORPORATION, Tokyo (JP)

(72) Inventor: Masahito Tanaka, Shimotsuke (JP)

(73) Assignee: KAO Corporation, Tokyo (JP)

( * ) Notice: Subject to any disclaimer, the term of this patent is extended or adjusted under 35 U.S.C. 154(b) by 223 days.

(21) Appl. No.: 14/100,766

(22) Filed: Dec. 9, 2013

(65) Prior Publication Data

US 2014/0163508 A1 Jun. 12, 2014

(30) Foreign Application Priority Data

Dec. 10, 2012 (JP) .................................. 2012-269477

(51) Int. Cl.
*A61F 13/47* (2006.01)
*A61F 13/514* (2006.01)
(Continued)

(52) U.S. Cl.
CPC .... *A61F 13/51478* (2013.01); *A61F 13/5146* (2013.01); *A61F 13/51405* (2013.01);
(Continued)

(58) Field of Classification Search
CPC .............. A61F 13/514; A61F 13/51405; A61F 13/51458; A61F 13/5146; A61F 13/535; A61F 2013/530875
See application file for complete search history.

(56) References Cited

U.S. PATENT DOCUMENTS 5,296,282 A * 3/1994 Evers ......................... 428/195.1
5,300,358 A * 4/1994 Evers ............................ 442/396
(Continued)

FOREIGN PATENT DOCUMENTS

JP        8-504474 A     5/1996
JP     2000-140016 A    5/2000
(Continued)

OTHER PUBLICATIONS

Extended European Search Report, dated Apr. 17, 2014, for European Application No. 13195277.2.

*Primary Examiner* — Kathryn E Ditmer
(74) *Attorney, Agent, or Firm* — Birch, Stewart, Kolasch & Birch, LLP (57) ABSTRACT

An absorbent member containing a hydrophobic material subjected to hydrophilic treatment, a plurality of through holes passing through the absorbent member in a thickness direction formed at a portion of the absorbent member in a target region (P). The absorbent member has a layer-stacked structure of a plurality of layers, stacked in the thickness direction. The Klemm water absorption height of a lower layer most proximal to the backsheet is higher than that of an upper layer most proximal to the topsheet. The backsheet contains a moisture permeable film including a plurality of microvoids, and having water repellent portions formed by water repellent finishing, on a portion in the target region (P) of a skin-facing surface of the moisture permeable film. A ratio of the total area of portions on which the water repellent finishing is performed to the area of the target region (P) is from 30% to 60%.

8 Claims, 2 Drawing Sheets

(51) Int. Cl.
  *A61F 13/53*    (2006.01)
  *A61F 13/535*   (2006.01)
  *A61F 13/537*   (2006.01)

(52) U.S. Cl.
  CPC .. *A61F 13/51462* (2013.01); *A61F 13/51484* (2013.01); *A61F 13/535* (2013.01); *A61F 13/53752* (2013.01); *A61F 2013/51409* (2013.01); *A61F 2013/51421* (2013.01); *A61F 2013/530452* (2013.01); *A61F 2013/53782* (2013.01); *A61F 2013/530802* (2013.01); *A61F 2013/530846* (2013.01); *A61F 2013/530875* (2013.01)

(56) References Cited

U.S. PATENT DOCUMENTS

| | | | | |
|---|---|---|---|---|
| 5,578,344 | A * | 11/1996 | Ahr et al. | 427/211 |
| 5,803,920 | A | 9/1998 | Gilman | |
| 6,152,906 | A * | 11/2000 | Faulks et al. | 604/385.01 |
| H0001969 | H * | 6/2001 | Fell et al. | 604/367 |
| 6,486,379 | B1 | 11/2002 | Chen et al. | |
| 6,570,059 | B1 | 5/2003 | Carlucci et al. | |
| 2001/0039406 | A1 * | 11/2001 | Hamajima et al. | 604/367 |
| 2002/0026169 | A1 * | 2/2002 | Takai et al. | 604/378 |
| 2006/0122569 | A1 | 6/2006 | Drevik et al. | |
| 2008/0294139 | A1 * | 11/2008 | Ecker et al. | 604/385.23 |
| 2009/0112173 | A1 | 4/2009 | Bissah et al. | |
| 2009/0112176 | A1 | 4/2009 | Austin et al. | |

FOREIGN PATENT DOCUMENTS

| | | |
|---|---|---|
| JP | 2004-538019 A | 12/2004 |
| JP | 2011-104057 A | 6/2011 |
| WO | WO 94/13704 A1 | 6/1994 |
| WO | WO 9802609 A1 * | 1/1998 |
| WO | WO 01/72251 A1 | 10/2001 |

* cited by examiner

Fig. 4

ABSORBENT ARTICLE WITH KLEMM GRADIENT AND WATER REPELLENT FINISHING

TECHNICAL FIELD

The present invention relates to an absorbent article such as a sanitary napkin.

BACKGROUND ART

An absorbent article that includes a topsheet forming a skin-facing surface, a backsheet forming a non-skin-facing surface, an absorbent member interposed between both the sheets, and a target region disposed so as to face an excretory part of a wearer when the wearer wears the absorbent article is widely used as an absorbent article such as a sanitary napkin. Further, to prevent stuffiness while a wearer wears the absorbent article, a liquid impermeable and moisture permeable film which includes microvoids penetrating the front and back surfaces thereof may be used as the backsheet in this type of absorbent article.

For example, JP 2000-140016 A discloses an absorbent article that a retaining adhesive for fixing clothing is applied on a non-skin-facing surface of a backsheet. A barrier layer made of a thermoplastic resin is provided on a portion of a non-skin-facing surface of the backsheet, which corresponds to the retaining adhesive, to prevent a disadvantage that the reduction of an adhesive force of the retaining adhesive is caused by the movement of the adhesive ingredient and the like of the retaining adhesive to the backsheet.

To prevent the exudation (wetting through) of liquid from a backsheet that is concern when a moisture permeable film is used as the backsheet, U.S. Pat. No. 6,570,059 (B1) discloses an absorbent article in which a backsheet is formed of first and second layers having moisture permeability and a plurality of capillary tubes are formed in the first layer relatively proximal to an absorbent member so as to be inclined with respect to a thickness direction of the first layer.

Further, an absorbent article in which a porous body such as polyurethane foam is used as an absorbent member is proposed. Since the absorbent member formed of the porous body is excellent in elastic recovery, the absorbent member has characteristic in that the shape of the absorbent member is easily stabilized while a wearer wears the absorbent article and is hardly twisted. For example, JP 8-504474 A discloses that a hydrophilic, flexible, and non-ionic polymer foam structure formed of open cells connected to each other is applied to a lower layer (downstream storage/distribution layer) of a two-layer absorbent member. Since this porous body generally includes a hydrophobic material such as various polymers as a main ingredient, the porous body inherently has hydrophobicity. Accordingly, the porous body cannot be used as an absorbent member, which absorbs and retains liquid, as it is. Accordingly, it is necessary to perform hydrophilic treatment on the porous body to use the porous body as an absorbent member. JP 8-504474 A discloses that a non-ionic surfactant is used as a hydrophilizing agent for hydrophilic treatment of the porous body, and liquid containing the hydrophilizing agent is applied to the surface of the porous body.

SUMMARY OF INVENTION

According to the present invention, there is provided an absorbent article including: a topsheet that forms a skin-facing surface; a backsheet that forms a non-skin-facing surface; an absorbent member that is interposed between both the sheets; and a target region that is disposed so as to face an excretory part of a wearer when the wearer wears the absorbent article, wherein the absorbent member contains a hydrophobic material subjected to hydrophilic treatment, a plurality of through holes penetrating the absorbent member in a thickness direction are formed at a portion of the absorbent member that is located in the target region, the absorbent member has a layer-stacked structure in which a plurality of layers are stacked in the thickness direction, the Klemm water absorption height, which is measured according to JIS P8141, of a lower layer, which is most proximal to the backsheet, of the layer-stacked structure is higher than that of an upper layer that is most proximal to the topsheet, the backsheet contains a moisture permeable film that includes a plurality of microvoids, and has a water repellent portion, which is formed by means of water repellent finishing, on a portion located in the target region of a skin-facing surface of the moisture permeable film, and a ratio of the total area of portions on which the water repellent finishing is performed to the area of the target region is in the range of from 30% to 60%.

BRIEF DESCRIPTION OF DRAWINGS

FIG. 3(a) is a plan view of a part of a portion of the skin-facing surface that has been subjected to water repellent finishing, and FIG. 3(b) is an enlarged plan view enlarging and illustrating a part of FIG. 3(a).

DETAILED DESCRIPTION OF THE INVENTION

In the absorbent article such as a sanitary napkin, liquid residue needs to be not easily generated on the topsheet forming the skin-facing surface and a dry feeling of the skin-facing surface needs to be excellent. However, in the absorbent articles disclosed in JP 2000-140016 A, U.S. Pat. No. 6,570,059 (B1), and JP 8-504474 A, these requirements are not satisfied and there is a room for improvement in a dry feeling of the skin-facing surface.

Further, similar to the polymer foam structure disclosed in JP 8-504474 A, in an absorbent article using "an absorbent member that contains a hydrophobic material and is subjected to hydrophilic treatment" (hereinafter, referred to as a hydrophilic treatment-absorbent member), there is a concern that the hydrophilizing agent having been contained in the absorbent member is eluted in the body fluid temporarily absorbed and retained in the absorbent member, and the body fluid contains the hydrophilizing agent, so that the surface tension of the body fluid is reduced, the permeability of the body fluid increased, and the body fluid exudes from the backsheet to the outside of the absorbent article due to the high permeability. An absorbent article which is excellent in a dry feeling of the skin-facing surface and in which liquid does not easily exude from the backsheet is not provided yet.

The invention relates to an absorbent article that is excellent in a dry feeling of a skin-facing surface and in which liquid does not easily exude from the backsheet.

As a result of various kinds of examination on the absorbent article including the hydrophilic treatment-absorbent member, the inventors have obtained that the liquid absorption rate (liquid permeation rate) of the hydrophilic treatment-absorbent member tends to be lower than that of a general absorbent member containing a hydrophilic material such as pulp fiber as a main ingredient, and it is effective to employ the following structures 1 and 2 in improving this and further improving a dry feeling of the skin-facing surface (first knowledge).

Structure 1: a plurality of through holes penetrating the absorbent member in the thickness direction are formed at the portion of the hydrophilic treatment-absorbent member corresponding to the target region.

Structure 2: the hydrophilic treatment-absorbent member has a layer-stacked structure in which a plurality of layers are stacked in the thickness direction, and the capillary force of a lower layer, which is most proximal to the backsheet, of the layer-stacked structure is higher than that of an upper layer that is most proximal to the topsheet (the Klemm water absorption height, which is measured according to JIS P8141, of the lower layer is higher than that of an upper layer).

However, as a result of more detailed examination, the inventors have found that the elution of the hydrophilizing agent contained in the hydrophilic treatment-absorbent member is facilitated with the improvement of the liquid absorption rate (liquid permeation rate) in an absorbent article improved on the basis of the first knowledge, so that the exudation of liquid from the backsheet (moisture permeable film) easily occurs. That is, when the hydrophilizing agent elutes in the liquid concentrically absorbed and retained in a portion of the hydrophilic treatment-absorbent member which is located in the target region and on which liquid is concentrated, particularly, a portion, which is located on the side of the backsheet, of the portion, the capillary force of the liquid is reduced and the permeability of the liquid into small voids or holes is increased. As a result, a risk that liquid exudes to underwear through microvoids of the backsheet (moisture permeable film) is increased.

Accordingly, as a result of various kinds of examination to solve a new problem, the inventors have obtained a knowledge (second knowledge) in which it is effective to use a moisture permeable film including a plurality of microvoids as a backsheet and to apply hydrophobic ink to a portion, which corresponds to a target region (a region in which a plurality of through holes are formed), of the skin-facing surface of the moisture permeable film (a surface facing the hydrophilic treatment-absorbent member) by a gravure printing method to form water repellent portions. Since the gravure printing method makes ink partially adhere in a dot shape unlike a so-called solid coating-printing method that makes ink adhere to the entire printing region without voids, it is possible to maintain the moisture permeability of the moisture permeable film at a practically sufficient level when hydrophobic ink adheres to the moisture permeable film by this printing method.

The invention has been made on the basis of the above-mentioned knowledge, and provides an absorbent article including a topsheet that forms a skin-facing surface, a backsheet that forms a non-skin-facing surface and an absorbent member that is interposed between both the sheets, and a target region that is disposed so as to face an excretory part of a wearer when the wearer wears the absorbent article. The absorbent member contains a hydrophobic material subjected to hydrophilic treatment. A plurality of through holes penetrating the absorbent member in a thickness direction are formed at a portion of the absorbent member that is located in the target region. The absorbent member has a layer-stacked structure in which a plurality of layers are stacked in the thickness direction. The Klemm water absorption height, which is measured according to JIS P8141, of a lower layer, which is most proximal to the backsheet, of the layer-stacked structure is higher than that of an upper layer that is most proximal to the topsheet. The backsheet contains a moisture permeable film that includes a plurality of microvoids. The backsheet has a water repellent region, which is formed by means of water repellent finishing, on a portion located in the target region of a skin-facing surface of the moisture permeable film. A ratio of the total area of portions on which the water repellent finishing is performed to the area of the target region is in the range of from 30% to 60%.

According to the invention, there is provided an absorbent article that is excellent in a dry feeling of the skin-facing surface and in which liquid does not easily exude from the backsheet.

Figure 1:
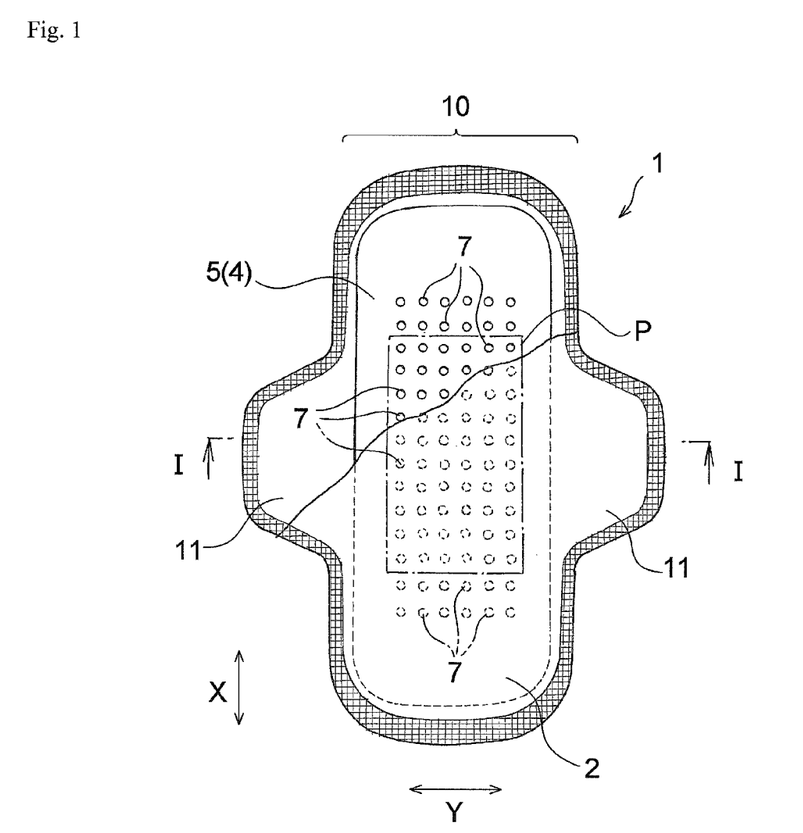
FIG. 1 is a plan view schematically illustrating a sanitary napkin which is an absorbent article according to a preferred embodiment of the invention and of which a part of a skin-facing surface (topsheet) is cut away.
Figure 2:
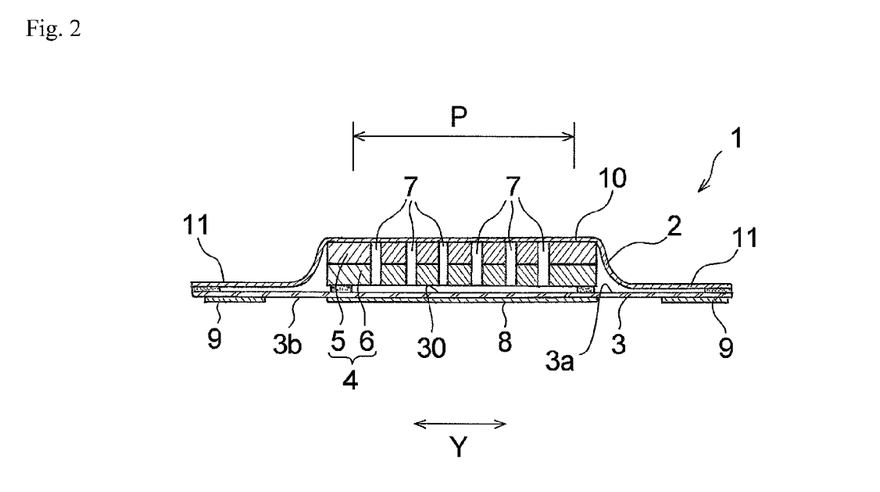
FIG. 2 is a cross-sectional view schematically illustrating the cross-section taken along line I-I of FIG. 1.

An absorbent article of the invention will be described below on the basis of a sanitary napkin, which is its preferred embodiment, with reference to the accompanying drawings. As illustrated in FIGS. 1 and 2, a napkin 1 of this embodiment includes a topsheet 2 that forms a skin-facing surface, a backsheet 3 that forms a non-skin-facing surface, and an absorbent member 4 that is interposed between both the sheets 2 and 3. Further, the napkin 1 includes a target region P that is disposed so as to face an excretory part of a wearer when the wearer wears the napkin. "When the wearer wears the napkin", which has been mentioned here, means a state in which a commonly appropriate wearing position (the right wearing position of the absorbent article) is maintained, and does not include a state in which the absorbent article deviates from the wearing position.

In detail, the napkin 1 includes an absorbent assembly 10 including the liquid permeable topsheet 2 that forms a skin-facing surface, the liquid impermeable backsheet 3 that forms a non-skin-facing surface, and the liquid retentive absorbent member 4 interposed between both the sheets 2 and 3. Further, the napkin 1 has a longitudinal direction X that corresponds to the front-rear direction of a wearer and a lateral direction Y that is orthogonal to the longitudinal direction X. The napkin 1 (absorbent assembly 10) has a shape oblong in one direction (longitudinal direction X) in plan view illustrated in FIG. 1, and is substantially longitudinally oblong. The topsheet 2 and the backsheet 3 are bonded to the absorbent member 4 by an adhesive that is applied to predetermined portions. The topsheet 2 and the backsheet 3 extend outward from the circumferential edge of the absorbent member 4, respectively, and form end seals by being bonded to each other at the ends of the extension portions of the topsheet 2 and the backsheet 3 by known bonding means, such as application of an adhesive or heat sealing.

Meanwhile, in this specification, the skin-facing surface is the surface of the absorbent article or a component thereof (for example, the absorbent assembly 10) that faces the wearer's skin when the wearer wears the absorbent article, and the non-skin-facing surface is the surface of the absorbent article or the component thereof that faces the side (clothing side) opposite to the skin when the wearer wears the absorbent article. Further, the longitudinal direction X corresponds to a direction (longer direction) parallel to the longer side of the absorbent article or the component thereof, and the lateral direction Y corresponds to a width direction of the absorbent article or the component thereof.

The napkin 1 includes a pair of wings 11 and 11 extending outward from both lateral side edges along the longitudinal direction X. The pair of wings 11 and 11 are formed to include extension portions that extend outward from both lateral side edges of the topsheet 2 and the backsheet 3 along the longitudinal direction X of the absorbent member 4. A non-skin-facing surface 3b of the backsheet 3, which forms the non-skin-facing surface of the napkin 1, is a surface that faces clothing, such as shorts, when a wearer wears the napkin, and adhesive parts 8 and 9, which fix the napkin 1 to the clothing, are provided on the non-skin-facing surface 3b as illustrated in FIG. 2. The adhesive part 8 is provided on the non-skin-facing surface of the absorbent assembly 10, and the adhesive parts 9 are provided on the non-skin-facing surfaces of the respective pair of wings 11 and 11. These adhesive parts 8 and 9 are provided by applying various adhesives, such as a hot melt adhesive, to predetermined portions, and are covered with release sheets (not illustrated), which are formed of films, nonwoven fabrics, paper, or the like, before the use of the napkin 1.

The target region of the invention is a region that has a center on a portion (target portion) of the absorbent article facing the excretory part (a vaginal opening or the like) of the wearer and has a rectangular shape having a length of 70 mm in the longitudinal direction X and a length of 30 mm in the lateral direction Y in plan view. The target portion is generally present at a center of the absorbent article in the longitudinal direction X or at a portion that is slightly closer to the front side (the front of a wearer) than the center.

The position of the target region of the invention can be specified by the wings or folding lines that are formed when the absorbent article is folded so as to be individually packaged. The napkin 1 of this embodiment includes the wings 11, and the target region P (a rectangular region surrounded by a one-dot chain line in FIG. 1) of the napkin 1 is present in a region in which the wings 11 are formed in the longitudinal direction X (a region formed between one root and the other root of the wing 11 in the longitudinal direction X). On the other hands, when the absorbent article does not include wings, a target region of the absorbent article is present in a region that is surrounded by first folding line and second folding line from a longitudinal front end of the absorbent article (a longitudinal end located on the front of a wearer) among two folding lines cross the absorbent article in the lateral direction which are formed when the absorbent article is folded into three sections so as to be individually packaged and which are parallel to each other. Further, when the length of an absorbent article in the longitudinal direction is long and three folding lines are formed, a target region of the absorbent article is present in a region that is surrounded by first and second folding lines from a longitudinal front end of the absorbent article or is present in a region that is surrounded by first and third folding lines from the longitudinal front end.

The absorbent member 4 contains a hydrophobic material that has been subjected to hydrophilic treatment. Various synthetic polymers can be used as the hydrophobic material that forms the absorbent member 4. The content of the hydrophobic material in the absorbent member 4 is preferably 60 mass % or more and more preferably 65 mass % or more based on the total mass of the absorbent member 4, and all materials of the absorbent member 4 may be formed of a hydrophobic material.

It is preferable that the form of the absorbent member 4 is a hydrophilic structure having a three-dimensional skeleton structure. Specifically, examples of the form of the absorbent member 4 include i) a form that includes a hydrophilic porous body (foam body) made of a hydrophobic material subjected to hydrophilic treatment and ii) a form that includes a hydrophilic fiber aggregate made of a fibrous hydrophobic material subjected to hydrophilic treatment. The absorbent member 4 may be a complex containing these both (the porous body and the fiber aggregate). In particular, the porous body (a foam material that is hydrophilic and has an open-cell structure) of i) has advantages in that a) the porous body is not easily twisted and is easily fitted to a human body since the porous body is soft and has elastic recovery and b) the porous body does not allow liquid to easily return or move and can stably absorb liquid since cells (foam) are not easily deformed even though human body pressure or motion deformation is applied to the porous body. Accordingly, since the porous body is excellent in the stable retention of liquid and the control of the spread of liquid when being used as the absorbent member, the porous body is preferably used as the absorbent member (layers forming the layer-stacked structure of the absorbent member to be described below) of the invention.

Materials known as the material of the porous body can be used as the hydrophobic material (synthetic polymer), which forms the porous body, without being particularly limited. Examples of the hydrophobic material include polyurethane, polystyrene, polyethylene, polyester, polyvinyl alcohol, styrene butadiene rubber (SBR), nitrile butadiene rubber, acrylic acid and a derivative thereof, a methacrylic acid and a derivative thereof, and a melamine resin. One of them can be used alone, or the combination of two or more of them can be used. Further, for example, various methods of forming foam, such as physical foaming using the blowing of a gas such as a carbon dioxide gas or nitrogen, supercritical foaming, the formation of a gap by an extraction method, the formation of foam in a method of performing polymerization after the formation of an emulsion such as a high internal phase emulsion foam, and the like other than the formation of foam by chemical foaming, such as urethane foam, can be used as a method of forming the porous body. A foam material disclosed in JP 8-504474 A can also be used as the porous body.

As for ii), examples of the form of a fiber aggregate include various nonwoven fabrics, such as an air-through nonwoven fabric, a heat roll nonwoven fabric, a spunbond nonwoven fabric, a resin bonded nonwoven fabric, a needle-punched nonwoven fabric, a spunlace nonwoven fabric, and an airlaid nonwoven fabric. Further, various known materials can be used as the fibrous hydrophobic material (synthetic polymer), which forms the fiber aggregate, without being particularly limited. Examples of the fibrous hydrophobic material include polyolefin resins, such as polyethylene and polypropylene, and polyester resins, such as polyethylene terephthalate. One of them can be used alone, or the combination of two or more of them can be used. The fibrous hydrophobic material may be a conjugated fiber or a single fiber that is made of one type of synthetic polymer or a blend polymer in which two or more types of synthetic polymers are mixed with each other. The conjugated fiber described above is a synthetic fiber that is obtained by conjugating two or more types of synthetic polymers having different ingredients from each other by a spinneret and by spinning the synthetic polymers, and is a fiber that has a structure in which the plurality of ingredients are continued in the longitudinal direction of the fiber and are bonded to each other in the fiber. The form of the conjugated fiber includes a core-sheath type, a side-by-side type, and the like, and is not particularly limited. Typically, voids of fibers of a nonwoven fabric, which is formed by the airlaid lamination and air-through bonding of short fibers having a fiber length of about 4 mm, and a nonwoven fabric, which is formed by the card lamination and air-through bonding of staple subjected to three-time crimping and having a fiber length of 51 mm, are relatively and three-dimensionally uniform. The voids can be appropriately adjusted by thermal compression (heat press) or hot embossing in a desired pattern, which is preferable. Further, if latent crimped fibers are appropriately mixed at the time of the card lamination in the latter, the density of a fiber is increased and the elastic recovery of a nonwoven fabric is improved by the crimp development of fibers at the time of air-through heating. Accordingly, it is preferable that latent crimped fibers be appropriately mixed at the time of the card lamination. Furthermore, a hydrophilic fiber may be mixed to any one of the nonwoven fabrics. A preferable fiber is a cellulose fiber, such as rayon, lyocell, or pulp. In order to obtain preferable wetting properties (twist/setting resistance) of the absorbent member 4, a mixing ratio of the hydrophilic fiber is preferably 30 mass % or less and is more preferably 20 mass % or less. In terms of a water absorption property, it is also advantageous to mix a hydrophilic fiber to only a lower layer or to increase the mixing ratio of a hydrophilic fiber in the lower layer.

As for ii), examples of a preferred embodiment of the absorbent member 4, which includes the fiber aggregate, include a member having a structure in which many granular absorbent polymers are interposed between two (upper and lower) nonwoven fabrics (fiber aggregates). In such a structure, the basis weight of the absorbent polymer is preferably 22 g/m$^2$ or more and more preferably 40 g/m$^2$ or more, and is preferably 130 g/m$^2$ or less and more preferably 90 g/m$^2$ or less. More specifically, the basis weight of the absorbent polymer is preferably in the range of from 22 g/m$^2$ to 130 g/m$^2$ and more preferably in the range of from 40 g/m$^2$ to 90 g/m$^2$. Further, the content of the absorbent polymer is preferably 20 mass % or more and more preferably 25 mass % or more based on the total mass of the absorbent member 4, and is preferably 50 mass % or less and more preferably 40 mass % or less based on the total mass of the absorbent member 4. More specifically, the content of the absorbent polymer is preferably in the range of from 20 mass % to 50 mass % and more preferably in the range of from 25 mass % to 40 mass % based on the total mass of the absorbent member 4.

Meanwhile, since the absorbent polymer not only is advantageous for the fixing and retention of absorbed body fluid but also has an effect of suppressing stuffiness by the reduction of equilibrium vapor pressure, and a merit, which is obtained when the absorbent polymer is applied to the absorbent member, is also large. However, since there are also demerits such as the complication of a structure and the increase of cost that are associated with the conjugation of polymers, the absorbent polymer may not be applied to the absorbent member.

The hydrophilic treatment of the hydrophobic material (synthetic polymer) forming the absorbent member 4 may be 1) a method of forming a hydrophobic structure (the porous body and the fiber aggregate), which has a three-dimensional skeleton structure, from the hydrophobic material and hydrophilizing the hydrophobic structure by applying a hydrophilizing agent to the hydrophobic structure, or may be 2) a method of hydrophilizing a hydrophobic material by applying a hydrophilizing agent to the hydrophobic material and forming a hydrophilic structure (the porous body and the fiber aggregate), which has a three-dimensional skeleton structure, from the hydrophobic material. Examples of the hydrophilizing agent include various alkyl sulfonate salts such as α-olefin sulfonate, acrylate, acrylate/acrylamide copolymer, ester amide, a salt of ester amide, polyethylene glycol and a derivative thereof, a water-soluble polyester resin, various silicone derivatives, various saccharide derivatives, and a mixture thereof. One of them can be used alone, or the combination of two or more of them can be used. Examples of a method of applying the hydrophilizing agent to the hydrophobic structure or the hydrophobic material (hydrophilic treatment method) include a method of applying the hydrophilizing agent by a known application method, and a method of immersing the hydrophobic structure or the hydrophobic material in the liquid containing the hydrophilizing agent.

The hydrophilizing agent may be applied to the entire hydrophobic structure (the porous body and the fiber aggregate) made of a hydrophobic material or may be applied to a part thereof. That is, the absorbent member 4 may be made of only hydrophobic material having been subjected to hydrophilic treatment, or may contain a hydrophobic material which has been subjected to hydrophilic treatment as a main ingredient and a hydrophobic material which have not been subjected to hydrophilic treatment, at a part thereof. In the case of the latter, it is preferable that a hydrophilizing agent be applied to at least the entire portion of the absorbent member 4 that is located in the target region P (a portion overlapping the target region P in plan view as illustrated in FIG. 1) (at least the entire portion of the absorbent member 4 that is located in the target region P be made of only the hydrophobic material having been subjected to hydrophilic treatment).

To ensure the stable absorption of liquid in the absorbent member 4, the content of the hydrophilizing agent of the absorbent member 4 is preferably 0.5 mass % or more, more preferably 0.75 mass % or more, and even more preferably 1 mass % or more based on the total mass of the absorbent member 4, and is preferably 2.5 mass % or less, more preferably 2 mass % or less, and even more preferably 1.7 mass % or less based on the total mass of the absorbent member 4. More specifically, the content of the hydrophilizing agent of the absorbent member 4 is preferably in the range of from 0.5 mass % to 2.5 mass %, more preferably in the range of from 0.75 mass % to 2 mass %, and even more preferably in the range of from 1 mass % to 1.7 mass % based on the total mass of the absorbent member 4.

Further, as illustrated in FIGS. 1 and 2, a plurality of through holes 7 penetrating the absorbent member 4 in a thickness direction are formed at the portion of the absorbent member 4 that is located in the target region P (the portion overlapping the target region P in plan view as illustrated in FIG. 1). The through holes 7 also contribute to the quick movement of much liquid or liquid having relatively high viscosity into the absorbent member 4. That is, when being humid, the absorbent member 4 containing a hydrophobic material has an elastic modulus change smaller than the elastic modulus change of an absorbent structure that contains a hydrophilic material, such as pulp, as a main ingredient, and can form a stable absorbent structure regardless of a usage environment. On the other hand, a property of the absorbent member 4, which causes a flexible structural change by the absorption of liquid, is very low. In particular, a flexible structural change at the time of the absorption of liquid is hardly obtained in the case of a form that includes the hydrophilic porous body (foam body) of i) made of a hydrophobic material having been subjected to hydrophilic treatment. Accordingly, since the through holes 7 are formed, liquid is temporarily stored in the through holes 7 and is easily and quickly distributed to the lower layer having a higher capillary force. Furthermore, since the through holes 7 are empty holes that do not retain liquid in most use situations, the formation of the through holes 7 is particularly effective in directly discharging the moisture of the skin-facing surface of the napkin 1 (the skin-facing surface of the topsheet 2) to the outside through the backsheet 3 and improving a dry feeling.

In this embodiment, each of the plurality of through holes 7 has a circular shape in plan view. Further, since the absorbent member 4 has a layer-stacked structure of an upper layer 5 and a lower layer 6 in this embodiment as described below, the plurality of through holes 7 penetrate the upper and lower layers 5 and 6 in the thickness direction. Accordingly, a skin-facing surface (a surface facing the topsheet 2) and a non-skin-facing surface (a surface facing the backsheet) of the absorbent member 4 communicate with each other through the through holes 7. As illustrated in FIG. 1, the through holes 7 are formed not only at the portion of the absorbent member 4, which is located in the target region P but also at portions of the absorbent member 4 that is not located in the target region P (portions not overlapping the target region P in plan view as illustrated in FIG. 1). The formation pattern of the through holes 7 of this embodiment is a pattern in which the plurality of through holes 7 are formed at regular intervals in the longitudinal direction X and form through-hole lines and the plurality of through-hole lines are formed at regular intervals in the lateral direction Y.

It is preferable that the through holes 7 have a diameter smaller than the thickness of the absorbent member 4 (a layer-stacked structure to be described below) as illustrated in FIG. 2 since the possibility that the liquid temporarily stored in the through holes 7 is absorbed in the surrounding absorbent member 4 before reaching the bottom portions of the through holes 7 is increased. The through holes 7 can be formed in an absorbent member (a layer-stacked structure) in which through holes are not formed by a method of performing hot embossing in a usual manner, a method of forming a hole with a heated pin, a method of trimming a hole in a non-heated compressed state, or the like. A preferred method of clearly forming the through hole 7 is the method of forming a hole with a heated pin having a predetermined shape and the method of trimming a hole in a non-heated compressed state.

It is preferable that the dimension of the through hole 7 and the like be set in the following manner in terms of effects (the improvement of a dry feeling of the skin-facing surface, and the like) caused by the formation of the through holes 7.

The diameter of the through hole 7 is preferably 1 mm or more and more preferably 1.5 mm or more, and is preferably 3 mm or less and more preferably 2 mm or less. More specifically, the diameter of the through hole 7 is preferably in the range of from 1 mm to 3 mm and more preferably in the range of from 1.5 mm to 2 mm.

The number of the through holes 7 present in a unit area, which corresponds to an area of one square centimeter and has a square shape in plan view, is preferably 3 or more and more preferably 4 or more, and is preferably 8 or less and more preferably 7 or less. More specifically, the number of the through holes 7 present in the unit area is preferably in the range of from 3 to 8 and more preferably in the range of from 4 to 7.

Moreover, as illustrated in FIG. 2, the absorbent member 4 has a layer-stacked structure in which a plurality of layers are stacked in the thickness direction. More specifically, the upper layer 5 and the lower layer 6 are sequentially stacked in an order proximal to the topsheet 2 (in an order distal to the backsheet 3), so that the absorbent member 4 is formed so as to have a two-layer structure. Since the shape and size (area) of the upper layer 5 in plan view are the same as those of the lower layer 6 in plan view, the upper and lower layers 5 and 6 completely correspond to each other in plan view of FIG. 1. Since the respective layers (upper and lower layers 5 and 6) of the layer-stacked structure are bonded to each other, the respective layers are inseparably integrated with each other. The respective layers of the layer-stacked structure of the absorbent member 4 may be integrated with each other, or a plurality of separate layers are stacked and upper and lower layers are integrally subjected to (dot) embossing so as to be thermally bonded to each other or may be bonded to each other by using bonding means such as an adhesive together. More specifically, the upper and lower layers 5 and 6 may be bonded to each other by hot embossing, or may be bonded to each other by an adhesive. When the respective layers (upper and lower layers 5 and 6) of the absorbent member 4 are bonded to each other by embossing, it is preferable that an embossed portion formed by the embossing does not penetrate the absorbent member 4.

The appropriate range of the basis weight of the absorbent member 4 (upper and lower layers 5 and 6) varies according to the form of the absorbent member 4 (upper and lower layers 5 and 6). In any case in which the absorbent member 4 (upper and lower layers 5 and 6) is the porous body of i) and in which the absorbent member 4 is the fiber aggregate of ii), it is preferable that the basis weight of each of the layers be set as follows.

The basis weight of the upper layer 5 (porous body) is preferably 70 g/m$^2$ or more and more preferably 100 g/m$^2$ or more, and is preferably 250 g/m$^2$ or less and more preferably 200 g/m$^2$ or less. More specifically, the basis weight of the upper layer 5 is preferably in the range of from 70 g/m$^2$ to 250 g/m$^2$ and more preferably in the range of from 100 g/m$^2$ to 200 g/m$^2$.

The basis weight of the lower layer 6 (porous body) is preferably 50 g/m$^2$ or more and more preferably 70 g/m$^2$ or more, and is preferably 200 g/m$^2$ or less and more preferably 150 g/m$^2$ or less. More specifically, the basis weight of the lower layer 6 is preferably in the range of from 50 g/m$^2$ to 200 g/m$^2$ and more preferably in the range of from 70 g/m$^2$ to 150 g/m$^2$.

A ratio of the basis weight of the upper layer 5 (porous body) to the basis weight of the lower layer 6 (porous body) (the basis weight of the upper layer/the basis weight of the lower layer) is preferably 1.3 or more and more preferably 1.5 or more, and is preferably 3 or less and more preferably 2.5 or less. Specifically, the ratio of the basis weight of the upper layer 5 to the basis weight of the lower layer 6 is preferably in the range of from 1.3 to 3 and more preferably in the range of from 1.5 to 2.5.

Further, the Klemm water absorption height, which is measured according to JIS P8141, of the lower layer 6, which is most proximal to the backsheet 3, of the layer-stacked structure (two-layer structure) of the absorbent member 4 is higher than that of the upper layer 5 that is most proximal to the topsheet 2. That is, the capillary force of the lower layer 6 is larger than that of the upper layer 5. Since the absorbent member 4 has such gradient of capillary force, together with the operation of the through holes 7, body fluid such as menstrual blood which is moved to the upper layer 5 through the topsheet 2 is not spread so much in a surface direction (a direction perpendicular to the thickness direction) in the upper layer 5 of which the capillary force is relatively small, is moved to the lower layer 6 without remaining so much in the upper layer 5, and is reliably retained in the lower layer 6 of which the capillary force is relatively larger. The liquid absorption characteristics of the absorbent member 4 are particularly effective in improving a dry feeling of the skin-facing surface of the napkin 1 (the skin-facing surface of the topsheet 2).

The Klemm water absorption height of the upper layer 5 is preferably 10 mm or more and more preferably 15 mm or more, and is preferably 50 mm or less and more preferably 40 mm or less. More specifically, the Klemm water absorption height of the upper layer 5 is preferably in the range of 10 mm to 50 mm and more preferably in the range of 15 mm to 40 mm.

The Klemm water absorption height of the lower layer 6 is preferably 30 mm or more and more preferably 45 mm or more. Meanwhile, the upper limit of the Klemm water absorption height of the lower layer 6 is not limited, but is preferably 120 mm or less.

A ratio of the Klemm water absorption height of the lower layer 6 to the Klemm water absorption height of the upper layer 5 (the Klemm water absorption height of the lower layer 6/the Klemm water absorption height of the upper layer 5) is preferably 1.7 or more, more preferably 2 or more, and even more preferably 2.2 or more.

The Klemm water absorption height of each of the layers (upper and lower layers 5 and 6) of the layer-stacked structure of the absorbent member is measured by the following method.

<Method of Measuring Klemm Water Absorption Height>

A layer to be measured is attentively taken out from the layer-stacked structure of the absorbent member as a sample so that the thickness of the layer is not changed, and the Klemm water absorption height of the layer is measured according to a test method of JIS P8141. Specifically, the sample is cut to a width of 10 mm and a length of 150 mm or more. A cutting method that may crush a sample, such as a method using a push cutter, is not preferable since there is a high possibility that the method affects a result when the sample is cut. For this reason, when the sample is cut, the sample is cut by a knife, a cutter, or a razor so that the cross-section of the sample is not crushed. Meanwhile, to avoid the influence of the through holes that are formed in the absorbent member, it is preferable that sampling be performed at a portion in which the through holes are not formed. When measurement is unavoidably performed at a portion in which the through holes are formed, that effect is added to the measurement result. Further, even when a sample having a sufficient length is not taken out from the layer-stacked structure of the absorbent member due to the influence of the length of a product and the through holes, measurement is performed with the possible length of a sample and that effect is added to the measurement result. Next, a cut sample is set on a jig prescribed in JIS P8141, a physiological saline of which the concentration of blue No. 1 (dye) is 0.02 mass % is used as a test solution, and the Klemm water absorption height of the sample after 10 minutes is measured. The above-mentioned measurement is performed five times, and an average value of the measured heights is used as a Klemm water absorption height. Meanwhile, measurement environment is 20° C. and 65% RH according to JIS P8141, but measurement can be performed in the ranges of 20±1° C. and 65±3% RH. Further, the sample, the jig, and the test solution, which have been used in the measurement, are used in the measurement after being kept for a whole day and night under the same environment.

Examples of a method of making the Klemm water absorption height of the lower layer 6 higher than that of the upper layer 5 (making the capillary force of the lower layer 6 larger than that of the upper layer 5) include a method of making the spatial capacity of a plurality of spaces of the lower layer 6 [cells (foam) of the porous body, voids between the fibers of the fiber aggregate, and the like] smaller than that of the upper layer 5 (hereinafter, referred to as a method A of adjusting a Klemm water absorption height) and a method of making the hydrophilicity of the lower layer 6 higher than that of the upper layer 5 (hereinafter, referred to as a method B of adjusting a Klemm water absorption height).

As for the method A of adjusting a Klemm water absorption height, when the absorbent member 4 (upper and lower layers 5 and 6) is the porous body (foam body) of i), the diameter of the cell of the porous body forming the lower layer 6 is made smaller than that of the upper layer 5. Such an adjustment of the diameter of the cell can be performed by making an expansion ratio vary when the porous body is manufactured using the upper and lower layers 5 and 6.

A ratio of the diameter of the cell of the porous body forming the upper layer 5 to the diameter of the cell of the porous body forming the lower layer 6 (the diameter of the cell of the upper layer 5/the diameter of the cell of the lower layer 6) is preferably 1.7 or more and more preferably 2 or more, and is preferably 10 or less and more preferably 8 or less. More specifically, this ratio is preferably in the range of from 1.7 to 10 and more preferably in the range of from 2 to 8.

The diameter of the cell of the upper layer 5 (porous body) is preferably 35 μm or more and more preferably 40 μm or more, and is preferably 120 μm or less and more preferably 100 μm or less. More specifically, the diameter of the cell of the upper layer 5 is preferably in the range of 35 μm to 120 μm and more preferably in the range of 40 μm to 100 μm.

The diameter of the cell of the lower layer 6 (porous body) is preferably 10 μm or more and more preferably 17 μm or more, and is preferably 40 μm or less and more preferably 30 μm or less. More specifically, the diameter of the cell of the lower layer 6 is preferably in the range of from 10 μm to 40 μm and more preferably in the range of from 17 μm to 30 μm.

Meanwhile, the diameter of the cell of the porous bodies (upper and lower layers 5 and 6) can be measured in a usual manner by an enlargement-observation system, such as an electron microscope or a microscope, that can display an actual size, preferably, can perform print. Specifically, a porous body to be measured is cut to a size, which can be placed on a stage, by a razor or the like not so as to be compressed in a thickness direction, and is enlarged and displayed on a monitor in a non-compressed state as described above. A measurement magnification can be arbitrarily selected in consideration of the size of the cell of a foam material, and is generally in the range of from about 100 to 500. Further, when the cell has a circular shape, the diameter of the circular cell is used as the diameter of the cell. When the cell has an elliptical shape, the minor axis diameter of the elliptical cell is used as the diameter of the cell. An average value of the diameters of twenties arbitrary cells of the porous body is used as the diameter of the cell of the porous body.

Furthermore, as for the method A of adjusting a Klemm water absorption height, when the absorbent member 4 (upper and lower layers 5 and 6) is the fiber aggregate of ii), the void between the fibers of the fiber aggregate forming the lower layer 6 is set smaller than the void between the fibers of the fiber aggregate forming the upper layer 5. Such an adjustment of the void between the fibers can be performed by making the thickness of a fibrous hydrophobic material (synthetic polymer) forming the lower layer 6 smaller than the thickness of a fibrous hydrophobic material forming the upper layer 5.

A ratio of the thickness of the fibrous hydrophobic material forming the upper layer 5, which is formed of an fiber aggregate, to the thickness of the fibrous hydrophobic material forming the lower layer 6, which is formed of an fiber aggregate, (the thickness of the fibrous hydrophobic material of the upper layer 5/the thickness of the fibrous hydrophobic material of the lower layer 6) is preferably 2 or more and more preferably 3.2 or more, and is preferably 8 or less and more preferably 6.5 or less. More specifically, this ratio is preferably in the range of from 2 to 8 and more preferably in the range of from 3.2 to 6.5.

The thickness of the fibrous hydrophobic material forming the upper layer 5 (fiber aggregate) is preferably 4 dtex or more and more preferably 5 dtex or more, and is preferably 14 dtex or less and more preferably 11 dtex or less. More specifically, the thickness of the fibrous hydrophobic material forming the upper layer 5 is preferably in the range of from 4 dtex to 14 dtex and more preferably in the range of from 5 dtex to 11 dtex.

The thickness of the fibrous hydrophobic material forming the lower layer 6 (fiber aggregate) is preferably 1.2 dtex or more and more preferably 1.8 dtex or more, and is preferably 4 dtex or less and more preferably 3 dtex or less. Examples of a specific example of a preferred embodiment of the lower layer 6 (fiber aggregate) include an aggregate of a fibrous hydrophobic material that has a thickness of 3 dtex or less. Further, it is also preferable that the aggregate (lower layer 6) of such a fibrous hydrophobic material be conjugated to the upper layer 5 (fiber aggregate) while being compressed in advance by hot embossing (in a dot shape or the like).

Meanwhile, the method B of adjusting a Klemm water absorption height (a method of making the hydrophilicity of the lower layer 6 higher than that of the upper layer 5) can be applied regardless of whether the absorbent member 4 (upper and lower layers 5 and 6) is the porous body (foam body) of i) or the fiber aggregate of ii), and the method B of adjusting a Klemm water absorption height can also be used together with the method A of adjusting a Klemm water absorption height. The method B of adjusting a Klemm water absorption height can be performed by making the content of a hydrophilizing agent, which is used in the hydrophilic treatment of the hydrophobic material of the lower layer 6, higher than that of the upper layer 5. More specifically, a hydrophobic layer-stacked structure made of a hydrophobic material is formed; a hydrophilizing agent is applied from the side of the lower layer 6 of the layer-stacked structure (a layer that is most proximal to the backsheet 3) when built in the napkin 1 by a known application method such as kiss coating or gravure coating; and the hydrophobic layer-stacked structure is dried. The hydrophilizing agent is not applied from the side of the upper layer 5 of the layer-stacked structure (a layer that is most proximal to the topsheet 2) when built in the napkin 1.

The content of the hydrophilizing agent of the lower layer 6 becomes higher than that of the upper layer 5 by such a method of applying the hydrophilizing agent, so that the hydrophilicity of the lower layer 6 becomes higher than that of the upper layer 5.

Further, when the hydrophilizing agent is applied from the side of the lower layer 6 (a lower layer side) of the hydrophobic layer-stacked structure made of the hydrophobic material as described above when built in the napkin 1, the hydrophilizing agent may be applied to the entire surface of the lower layer side or the hydrophilizing agent may be partially applied to only a portion of the lower layer side which corresponds to the target region P (a portion overlapping the target region P in plan view illustrated in FIG. 1). The application form of the latter can be achieved by applying the hydrophilizing agent with a narrow application roller of which the length in the lateral direction Y is shorter than that length of the absorbent member 4 (lower layer 6) in the lateral direction Y. In the lower layer 6 that is obtained by the application form of the latter, the middle portion (a portion corresponding to the target region P) in the lateral direction Y has relatively high hydrophilicity but both side portions provided on both sides of the middle portion in the lateral direction Y has relatively low hydrophilicity or hydrophobicity. Accordingly, the movement of liquid to both the side portions from the middle portion is more effectively suppressed. Eventually, the exudation of liquid from the backsheet is prevented.

Since the absorbent member 4 has the above-mentioned structure (the structures 1 and 2), the napkin 1 of this embodiment has a high liquid absorption rate (liquid permeation rate) and is excellent in a dry feeling of the skin-facing surface (topsheet 2). On the other hand, as the performance of such an absorbent member 4 is improved, the elution of a hydrophilizing agent into the body fluid, which is absorbed and retained in the absorbent member 4, is facilitated as described above. Accordingly, the body fluid contains the hydrophilizing agent eluted from the absorbent member 4, so that the permeability of the body fluid is increased by the reduction of the surface tension. For this reason, there is a concern that a disadvantage that the body fluid exudes to the outside of the napkin 1 through the backsheet 3. That is, since the hydrophilicity of the absorbent member 4 tends to be reduced by the use of the absorbent member 4 (absorption and retention of liquid) as compared to a hydrophilic material such as rayon, the durability of hydrophilicity of the absorbent member 4 is low.

The durability of hydrophilicity of the absorbent member can be evaluated by the degree of the change of liquid droplet-absorption time that is measured by the following method. Initial liquid droplet-absorption time, which is measured by the following method, of the absorbent member 4 of which the durability of hydrophilicity is low is 3 seconds or less, and liquid droplet-absorption time after water washing and drying, which is measured by the following method, thereof is 30 seconds or more. In short, the absorbent member 4 of which the durability of hydrophilicity is low is washed with water and dried as described below, so that most of the hydrophilizing agent initially contained in the absorbent member 4 is eluted. Accordingly, hydrophilicity, which is given by the hydrophilic treatment using the hydrophilizing agent, deteriorates and the original characteristics of the hydrophobic material become significant. As a result, liquid absorbency deteriorates.

<Method of Measuring Liquid Droplet-Absorption Time (Method of Evaluating Durability of Hydrophilicity)>

One droplet (about 0.15 cc) of physiological saline is placed on the skin-facing surface of the absorbent member to be evaluated (the upper layer 5 of the absorbent member 4) by using a Komagome pipette or the like, and time, which is taken until the physiological saline is absorbed in the absorbent member and cannot be visually confirmed from immediately after the one droplet of physiological saline is placed, is measured. This time is used as the initial liquid droplet-absorption time. Further, a series of work for completely immersing a separate absorbent member to be evaluated in flowing water of 25° C. under the environment in which room temperature is 25° C., taking the absorbent member out of the flowing water after leaving the absorbent member for 20 seconds in this state, wringing the absorbent member by hands, and completely immersing the absorbent member in flowing water again are repeated three times. After that, the absorbent member is dried for one hour at a set temperature of 60° C. by a hot air drier, the liquid droplet-absorption time of the absorbent member, which has been subjected to water washing and drying and is obtained by such a washing process and a drying process, is measured in the same manner as described above, and a measured value thereof is used as the liquid droplet-absorption time after water washing and drying. Meanwhile, twenty droplets of physiological saline are placed at different positions on one sample, respectively, and an average of values of the absorption time, which are measured at the twenty positions, is employed as each of the initial liquid droplet-absorption time and the liquid droplet-absorption time after water washing and drying.

Accordingly, in this embodiment, the above-mentioned concern is dispelled by devising the backsheet 3 as described below. That is, in this embodiment, the backsheet 3 is formed of a moisture permeable film that includes a plurality of microvoids, and water repellent finishing is performed on a portion, which is located in the target region P, of a skin-facing surface (a surface facing the absorbent member 4) 3a (see FIG. 2) of the moisture permeable film, so that water repellent portions 30 are formed. In this embodiment, the backsheet 3 is formed of only a single-layer moisture permeable film. Examples of a moisture permeable film, which is suitable as the backsheet 3, include a poromeric film that is formed by stretching a film (which is obtained by melting, kneading, and extruding a thermoplastic resin such as a polyolefin resin and fine particles of an inorganic filler not compatible with the thermoplastic resin) to predetermined dimensions and forming microvoids in the film. The plurality of microvoids are formed in the poromeric film, which is manufactured as described above, from interfaces between the thermoplastic resin and the fine particles of the inorganic filler as origins by stretching.

The water repellent portions 30 may be formed at a portion, which is located in the target region P, of the skin-facing surface 3a of the moisture permeable film (backsheet 3), and may be formed over the entire surface of the skin-facing surface 3a. However, the moisture permeability of the moisture permeable film tends to deteriorate with the increase of the area of the water repellent portions 30. Accordingly, to ensure the maintaining of practically sufficient moisture permeability of the moisture permeable film, it is preferable that the water repellent portions 30 be partially formed on the skin-facing surface 3a. In particular, it is more preferable that the water repellent portions 30 be formed only at a portion, which is located in the target region P, of the skin-facing surface 3a or only at the portion and vicinity of the portion. Examples of the formation pattern of the water repellent portions 30, which is partially formed on the skin-facing surface 3a, include a pattern in which a plurality of strip-shaped water repellent portions 30 extending in one direction (for example, the longitudinal direction X) are disposed at a predetermined interval in a direction (the lateral direction Y) orthogonal to the one direction. The width of the strip-shaped water repellent portion 30 (the length of the strip-shaped water repellent portion 30 in the lateral direction Y) is preferably 50 mm.

In this embodiment, the water repellent finishing for the moisture permeable film (backsheet 3) is performed by applying hydrophobic ink to the portion, which is located in the target region P, of the skin-facing surface 3a of the moisture permeable film by a gravure printing method, and the water repellent portions 30 are formed of portions to which the hydrophobic ink adheres. Since a gravure printing method applies hydrophobic ink in a dot-shaped (dispersed dot-shaped) printing pattern, a gravure printing method is suitable for appropriately controlling the liquid permeability and the moisture permeability of the backsheet 3 (moisture permeable film) by the adjustment of the printing area ratio of the dots or the like and also has a high aptitude for multicolor printing, unlike a so-called solid coating-printing method. Accordingly, the gravure printing method is suitably used as the water repellent finishing for the backsheet (moisture permeable film) of the invention.

Figure 3:
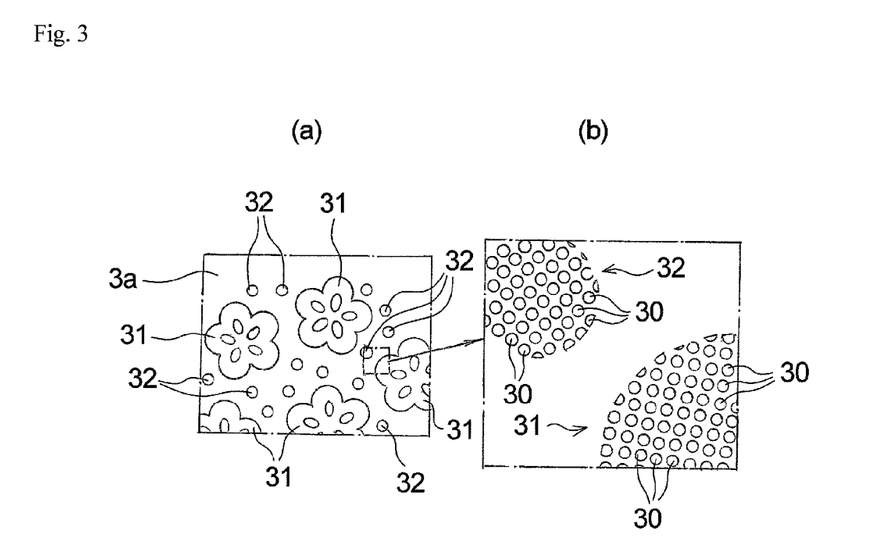
FIG. 3 is a view schematically illustrating an example of water repellent finishing for a skin-facing surface of a backsheet (moisture permeable film) that is performed by a gravure printing method.

An example of the water repellent finishing for the backsheet, which is performed by the gravure printing method, is illustrated in FIG. 3. In the embodiment illustrated in FIG. 3, as illustrated in FIG. 3($a$), hydrophobic ink is applied to a portion, which is located in the target region P, of the skin-facing surface 3a of the moisture permeable film (backsheet 3) by the gravure printing method and a plurality of petal patterns 31 and a plurality of circular patterns 32 are printed on the portion. Each of these printed patterns 31 and 32 is an aggregate of the water repellent portions 30 (portions to which the hydrophobic ink adheres) having a circular shape in plan view as illustrated in FIG. 3($b$), and each of the water repellent portions 30 of the aggregate is surrounded by a non-water repellent portion where hydrophobic ink does not adhere and water repellent finishing is not performed.

In this embodiment, in terms of a balance between the liquid permeability and the moisture permeability of the moisture permeable film (backsheet 3), a ratio of the total area of portions on which the water repellent finishing is performed to the area of the target region P, that is, a ratio of the total area of the portions to which the hydrophobic ink adheres (water repellent portions 30) to the area of the target region P (the total area of the plurality of water repellent portions 30/the area of the target region P) is in the range of from 30% to 60%. This ratio is preferably 35% or more and more preferably 40% or more, and is preferably 58% or less and more preferably 55% or less. More specifically, this ratio is preferably in the range of from 35% to 58% and more preferably in the range of from 40% to 55%.

If the non-water repellent portion is continuously present, a risk of the exudation of liquid of which the surface tension is reduced due to that the liquid contains the hydrophilizing agent eluted from the absorbent member 4 is increased. It is preferable that one or both of the following structures A and B be employed to reduce this risk.

Structure A: when each of the printed patterns 31 and 32 of the target region P, which includes the water repellent portions 30 (the portions to which the hydrophobic ink adheres) and the non-water repellent portion, is referred to as one printing area and other portions except for the printing area are referred to as non-printing areas, a ratio of the area of the non-printing areas (which is calculated by subtracting the sum of the areas of all the printing areas from the area of the target region P) to the area of the target region P (that is, a non-printing area ratio) is preferably 42% or less and more preferably 35% or less.

Structure B: when the target region P is divided into a plurality of divided areas of 10 mm×10 mm and the area of the non-water repellent portions continuing in each of the divided areas is measured, it is preferable that the number of the divided areas of which the area exceeds 50 mm$^2$ be 15% or less of the number of all of the divided areas and it is more preferable that the divided areas of which the area exceeds 50 mm$^2$ be not present. More preferably, the number of the divided areas of which the area exceeds 25 mm$^2$ is preferably 25% or less of the number of all of the divided areas and more preferably 18% or less thereof.

Further, from the same viewpoint, in regard to an arbitrary printed pattern (an arbitrary petal pattern 31 or an arbitrary circular pattern 32 in the embodiment illustrated in FIG. 3) that is printed on the skin-facing surface 3a of the moisture permeable film (backsheet 3) with hydrophobic ink, a ratio of the total area of the portions to which the hydrophobic ink adheres and which form the printed pattern (water repellent portions 30) to the area of the printed pattern (the total area of the plurality of water repellent portions 30/the area of one printed pattern formed by the plurality of water repellent portions 30) is preferably 40% or more and more preferably 45% or more, and is preferably 80% or less and more preferably 60% or less. More specifically, this ratio is preferably in the range of from 40% to 80% and more preferably in the range of from 45% to 60%.

Known hydrophobic ink, which can be applied to a general gravure printing method, such as evaporation-drying type ink, two-liquid reactive ink, and ultraviolet ray-curable ink can be used as the hydrophobic ink, which is used in the water repellent finishing for the moisture permeable film (backsheet 3), without being particularly limited. The hydrophobic ink may has a color or be colorless and transparent. When colored hydrophobic ink is used, the water repellent portions 30 have a color. In this embodiment, as described above, the plurality of through holes 7 penetrating the absorbent member 4 in the thickness direction are formed at the portion of the absorbent member 4 (upper and lower layers 5 and 6) that overlaps the water repellent portions 30 in the plan view of the napkin 1 as illustrated in FIG. 1. Accordingly, if the water repellent portions 30 have a color, the colored water repellent portions 30 can be visually recognized through the topsheet 2 and the plurality of through holes 7 of the absorbent member 4 when the napkin 1 is visually recognized from the topsheet 2 as illustrated in FIG. 1. Therefore, an effect of easily identifying a position where the napkin 1 is arranged is obtained, for example, when the napkin 1 is arranged on underwear.

The basis weight of the moisture permeable film (backsheet 3) is 18 g/m$^2$ or more. In terms of a balance between the prevention of stuffiness, which is caused by a lack of the moisture permeability amount, and the prevention of the exudation of liquid from the backsheet, which is caused by too much moisture permeability amount (microvoids), it is preferable that the moisture permeability amount in a portion of the moisture permeable film located in the target region P be in the range of from 1.0 g/(100 cm$^2$·hr) to 2.2 g/(100 cm$^2$·hr). In the water repellent finishing using the above-mentioned gravure printing method, it is possible to adjust the moisture permeability amount by appropriately adjusting the printing patterns of the hydrophobic ink and appropriately adjusting a ratio of the total area of the portions to which the hydrophobic ink adheres (water repellent portions 30) to the area of the target region P or, in regard to an arbitrary printed pattern that is printed on the skin-facing surface 3a of the moisture permeable film (backsheet 3) with hydrophobic ink, a ratio of the total area of the portions to which the hydrophobic ink adheres and which form the printed pattern (water repellent portions 30) to the area of the printed pattern. Further, if the basis weight of the moisture permeable film is excessively small, there is a possibility that a trouble that a break occurs during use. Accordingly, it is preferable that the moisture permeable film have a certain level of basis weight.

More specifically, the basis weight of the moisture permeable film, which forms the backsheet 3, is preferably 18 g/m$^2$ or more and more preferably 35 g/m$^2$ or more, and is preferably 50 g/m$^2$ or less and more preferably 45 g/m$^2$ or less. Even more specifically, the basis weight of the moisture permeable film is preferably in the range of from 25 g/m$^2$ to 50 g/m$^2$ and more preferably in the range of from 35 g/m$^2$ to 45 g/m$^2$. If the basis weight of the moisture permeable film, which forms the backsheet 3, is set in the above-mentioned range, it is easy to maintain the softness of the backsheet 3 while preventing the backsheet 3 from being broken against the adhesive forces of the adhesive parts 8 and 9 provided on the non-skin-facing surface 3b of the backsheet 3 when the napkin 1 is separated from clothing after being used.

Furthermore, the moisture permeability amount in a portion of the moisture permeable film, which is located in the target region P, is preferably 1.0 g/(100 cm$^2$·hr) or more and more preferably 1.5 g/(100 cm$^2$·hr) or more, and is preferably 2.2 g/(100 cm$^2$·hr) less and more preferably 2.0 g/(100 cm$^2$·hr) or less. More specifically, the moisture permeability amount the portion is preferably in the range of from 1.0 g/(100 cm$^2$·hr) to 2.2 g/(100 cm$^2$·hr) and more preferably in the range of from 1.5 g/(100 cm$^2$·hr) to 2.0 g/(100 cm$^2$·hr).

Meanwhile, the measurement of the moisture permeability amount was performed by a method (condition B: a temperature of 40±0.5° C. and a humidity of 90±2%) that is prescribed in a cup method of JIS Z-0208.

Meanwhile, when the absorbent article of the invention is a sanitary napkin like the napkin 1, the assumed amount of absorbed liquid is relatively small, that is, in the range of from about 2 to 7 g and the thickness of a region of a target region in which the absorbent member is disposed is small (the thickness in the case of the sanitary napkin is preferably 5 mm or less) as compared to another absorbent article (for example, a disposable diaper) for which the amount of absorbed liquid larger than this is required. Accordingly, when a moisture permeable backsheet is used, vapor present in the napkin or between the napkin and a wearer is sufficiently easily discharged to the outside of the napkin. In addition, since the covering area of the sanitary napkin covering a wearer's body is smaller than that of a disposable diaper that is designed to cover the entire wearer's crotch, the sanitary napkin can sufficiently give a dry feeling to the wearer even though the moisture permeability amount in the backsheet of the sanitary napkin is set smaller than that of the disposable diaper. Accordingly, when the moisture permeability amount in the portion, which is located in the target region P, of the moisture permeable film forming the backsheet 3 is set in the above-mentioned range, the exudation of menstrual blood containing the hydrophilizing agent from the backsheet 3 is also prevented and sufficient moisture permeability is ensured.

Other materials of the napkin 1 will be described. Various objects conventionally used in this technical field can be used as the topsheet 2 without being particularly limited. For example, various nonwoven fabrics subjected to hydrophilic treatment or a liquid permeable sheet such as a perforated film can be used as the topsheet 2. To quickly absorb excreted body fluid, transmit the body fluid to the absorbent member, and improve a feel to the touch, a hydrophilic thermal bond nonwoven fabric is preferable as the topsheet 2 and an air-through nonwoven fabric is particularly preferable as the topsheet 2. It is preferable that the topsheet 2 be made of a thermoplastic resin fiber subjected to hydrophilic treatment and be made of a fiber three-dimensionally crimped, that is, secondarily crimped or tertiarily crimped. Specifically, a polyethylene fiber, a polypropylene fiber, a polyester fiber, a nylon fiber, and a conjugated fiber thereof are formed and are cut to a predetermined length, and various hydrophilizing agents are applied to the fibers before the formation of staple.

The invention has been described above on the basis of a preferred embodiment thereof, but the invention is not limited to the embodiment. For example, the planar shape of the through hole is not limited to a circular shape, and may be various shapes, such as a quadrangular shape. Further, the formation pattern of the through holes is also not particularly limited, and may have a zigzag shape and the like. Furthermore, the skin-facing surface (a surface facing the topsheet 2) and the non-skin-facing surface (a surface facing the backsheet 3) of the absorbent member 4 may be covered with paper such as tissue paper, various nonwoven fabrics, a water permeable sheet such as a perforated film, or the like. Moreover, in the embodiment, a sanitary napkin has been exemplified as an example to which the absorbent article of the invention is applied. However, the absorbent article of the invention can also be applied to, for example, a panty liner (discharge sheet), an incontinence pad, a disposable diaper, and the like. Further, the absorbent member using the porous body (foam material) of i) also may be combined with an absorbent polymer in the same manner as the absorbent member using the fiber aggregate of ii).

The following additional statement (absorbent article) is disclosed in regard to the above-mentioned embodiment of the invention.

<1> An absorbent article comprising:
a topsheet that forms a skin-facing surface;
a backsheet that forms a non-skin-facing surface;
an absorbent member that is interposed between both the sheets; and
a target region that is disposed so as to face an excretory part of a wearer when the wearer wears the absorbent article,
wherein the absorbent member contains a hydrophobic material subjected to hydrophilic treatment,
a plurality of through holes penetrating the absorbent member in a thickness direction are formed at a portion of the absorbent member that is located in the target region,
the absorbent member has a layer-stacked structure in which a plurality of layers are stacked in the thickness direction,
the Klemm water absorption height, which is measured according to JIS P8141, of a lower layer, which is most proximal to the backsheet, of the layer-stacked structure is higher than that of an upper layer that is most proximal to the topsheet,
the backsheet comprises a moisture permeable film that includes a plurality of microvoids, and has a water repellent region, which is formed by means of water repellent finishing, on a portion located in the target region of a skin-facing surface of the moisture permeable film, and
a ratio of the total area of portions on which the water repellent finishing is performed to the area of the target region is in the range of from 30% to 60%.

<2> The absorbent article according to <1>,
wherein the water repellent finishing is performed by applying hydrophobic ink to the portion, which is located in the target region, of the skin-facing surface of the moisture permeable film by a gravure printing method, and
the water repellent portions are formed of portions to which the hydrophobic ink adheres.

<3> The absorbent article according to <1> or <2>,
wherein the basis weight of the moisture permeable film is 18 g/m$^2$ or more, and
the moisture permeability amount in the portion of the moisture permeable film located in the target region is in the range of from 1.0 g/(100 cm$^2$·hr) to 2.2 g/(100 cm$^2$·hr).

<4> The absorbent article according to any one of <1> to <3>,
wherein the absorbent member is a hydrophilic structure having a three-dimensional skeleton structure.

<5> The absorbent article according to <4>,
wherein the absorbent member includes a hydrophilic porous body made of a hydrophobic material subjected to hydrophilic treatment.

<6> The absorbent article according to <5>,
wherein the hydrophobic material forming the porous body is one or two or more of the group selected from polyurethane, polystyrene, polyethylene, polyester, polyvinyl alcohol, styrene butadiene rubber (SBR), nitrile butadiene rubber, acrylic acid and a derivative thereof, methacrylic acid and a derivative thereof, and a melamine resin.

<7> The absorbent article according to <5> or <6>,
wherein the basis weight of the upper layer is in the range of from 70 g/m$^2$ to 250 g/m$^2$.

<8> The absorbent article according to any one of <5> to <7>,
wherein the basis weight of the lower layer is in the range of from 50 g/m$^2$ to 200 g/m$^2$.

<9> The absorbent article according to any one of <5> to <8>,
wherein a ratio of the basis weight of the upper layer to the basis weight of the lower layer (the basis weight of the upper layer/the basis weight of the lower layer) is in the range of from 1.3 to 3.

<10> The absorbent article according to any one of <5> to <9>,
wherein a ratio of the diameter of a cell of the porous body forming the upper layer to the diameter of a cell of the porous body forming the lower layer (the diameter of a cell of the upper layer/the diameter of a cell of the lower layer) is in the range of from 1.7 to 10.

<11> The absorbent article according to <4>,
wherein the absorbent member includes a hydrophilic fiber aggregate made of a fibrous hydrophobic material subjected to the hydrophilic treatment.

<12> The absorbent article according to <11>,
wherein a ratio of the thickness of the fibrous hydrophobic material of the upper layer, which is formed of the fiber aggregate, to the thickness of the fibrous hydrophobic material of the lower layer, which is formed of the fiber aggregate, (the thickness of the fibrous hydrophobic material of the upper layer/the thickness of the fibrous hydrophobic material of the lower layer) is preferably in the range of from 2 to 8.

<13> The absorbent article according to any one of <1> to <12>,
wherein the Klemm water absorption height of the upper layer is in the range of from 10 mm to 50 mm.
<14> The absorbent article according to any one of <1> to <13>,
wherein the Klemm water absorption height of the lower layer is 30 mm or more.
<15> The absorbent article according to any one of <1> to <14>,
wherein a hydrophilizing agent used in the hydrophilic treatment is applied to the entire hydrophobic structure (the porous body and the fiber aggregate) made of a hydrophobic material.
<16> The absorbent article according to any one of <1> to <15>,
wherein a portion of the absorbent member located in the target region is made of only a hydrophobic material subjected to the hydrophilic treatment.
<17> The absorbent article according to any one of <1> to <16>,
wherein the diameter of the through hole is smaller than the thickness of the absorbent member (the layer-stacked structure).
<18> The absorbent article according to any one of <1> to <17>,
wherein the upper layer and lower layer are bonded to each other by hot embossing.
<19> The absorbent article according to <18>,
wherein an embossed portion formed by the hot embossing does not penetrate the absorbent member.
<20> The absorbent article according to any one of <1> to <17>,
wherein the upper layer and lower layer are bonded to each other by an adhesive.
<21> The absorbent article according to any one of <1> to <20>,
wherein the absorbent article is a sanitary napkin

EXAMPLES

The invention will be described in more detail with reference to examples, but the invention is not limited to the examples.

Example 1

A sanitary napkin, which has the same structure as the sanitary napkin illustrated in FIGS. 1 and 2, was produced and was referred to as a sample of Example 1. Meanwhile, sheets having the following structure were used as a topsheet and a backsheet, and the following porous body A having a layer-stacked structure (two-layer structure) was used as an absorbent member.

Topsheet: a hydrophilic air-through nonwoven fabric having a basis weight of 25 g/m$^2$.

Backsheet: a sheet having water repellent portions obtained by performing water repellent finishing on one surface (a surface that forms a skin-facing surface when built in the napkin) of a single-layer moisture permeable film that has a basis weight of 40 g/m$^2$ and the moisture permeability amount (the moisture permeability amount before water repellent finishing) of 2.1 g/(100 cm$^2$·hr) and which includes a plurality of microvoids. The water repellent finishing was performed as follows. That is, dot printing, which had the number of lines (print density) of 50 lpi and a printing area ratio of 50%, was performed on the entire surface of the moisture permeable film with ink "HIGH PRINT J" cyan, which was manufactured by Dainichiseika Colour & Chemicals Mfg. Co., Ltd., as hydrophobic (water repellent) gravure printing ink by a gravure printing method; and water repellent portions formed of the portion to which the hydrophobic ink adheres were formed. Meanwhile, screentone No. 55 of Letraset (Esselte Corporation) was employed when printed dots were set. The "printing area ratio", which has been mentioned here, corresponds to the above-mentioned "ratio of the total area of the portions to which the hydrophobic ink adheres (water repellent portions) and which form an arbitrary printed pattern to the area of the printed pattern" (the total area of a plurality of water repellent portions 30/the area of one printed pattern formed by the plurality of water repellent portions 30), and corresponds to the above-mentioned "ratio of the total area of the portions to which the hydrophobic ink adheres (water repellent portions) to the area of the target region" (the total area of the plurality of water repellent portions 30/the area of the target region P), that is, a "ratio of the total area of the portions on which the water repellent finishing is performed to the area of the target region".

(Preparation of Porous Body A)

A foam material A (a sample of urethane foam HSS-2000 having a predetermined basis weight, manufactured by INOAC Corporation) and a foam material B (a sample of a polyolefin foam (elution method) ST-15 having a predetermined basis weight, manufactured by INOAC Corporation) were used as raw materials. The foam material A is a raw material of the upper layer of the layer-stacked structure (two-layer structure) forming the absorbent member, and the foam material B is a raw material of the lower layer of the layer-stacked structure. Meanwhile, to eliminate the influence of residues of material adhesion/a process oil agent, and the like, all of the foam materials A and B were washed and dried according to the washing process and the drying process described in the <method of measuring liquid droplet-absorption time (the method of evaluating the durability of hydrophilicity)>. Then, all of the foam materials A and B were supplied to the following preparation. The preparation of the porous body A was performed as follows. First, after the foam material A (having a basis weight of 100 g/m$^2$) and the foam material B (having a basis weight of 120 g/m$^2$) were cut to a size having a length of 195 mm and a width of 75 mm and superimposed, hot embossing was uniformly performed over the entire surfaces of the superimposed foam materials A and B at a temperature of 140° C. with a contact pressure of 15 kg for 1 second by pin-like members having a diameter of 1.5 mm and a pitch of 8 mm between the pins. Accordingly, the foam materials A and B were compressed and integrated with each other, so that a precursor of a porous body was obtained. The entire precursor was immersed in an aqueous solution of a separately prepared hydrophilizing agent (an aqueous solution containing 0.75 mass % of alkyl glycoside) for sufficient time. The precursor was lifted from the aqueous solution, was wrung so that the aqueous solution having substantially the same weight as the precursor adheres to the precursor, and was dried at 60° C. for 8 hours by using electricity. Through holes having a diameter of 1.5 mm were uniformly trimmed and formed by a hollow punch at a position corresponding to the target region in a region of the dried precursor that has a rectangular shape in plan view and has a length of 80 mm in the longitudinal direction X and a length of 40 mm in the lateral direction Y so that the number of holes formed in the square area of one square centimeter was 4. The precursor in which the through holes were formed as described above was referred to as a porous body A. Meanwhile, Midol 10 (effective ingredient 40%) manufactured by Kao Corporation was used as alkyl glycoside.

Example 2

A sanitary napkin was produced in the same manner as Example 1 except that the following porous body B having a layer-stacked structure (two-layer structure) was used as the absorbent member, and was referred to as a sample of Example 2.
(Preparation of Porous Body B)

A porous body B was obtained in the same manner as the (Preparation of porous body A) except that, as described below, a precursor of a porous body is obtained by non-compression and integration using a hot melt adhesive under specific conditions instead of compression and integration of the foam material A (having a basis weight of 100 g/m$^2$) and the foam material B (having a basis weight of 120 g/m$^2$) performed by hot embossing bonding in the (Preparation of the porous body A), and hydrophilic treatment was performed from the non-skin-facing surface of the precursor of a porous body. The adhesion between the foam materials A and B was performed by directly spirally spraying a rubber hot-melt adhesive on one surface of the foam material A so that a basis weight of the adhesive becomes 15 g/m$^2$, and by bonding the foam material B to the surface on which the adhesive was sprayed. As a result, the precursor of a porous body was obtained. Further, hydrophilic treatment for the precursor of a porous body, which was obtained in this way, was performed by uniformly applying a hydrophilizing agent aqueous solution, which was obtained by changing the concentration of alkyl glycoside to 7.5 mass % in the hydrophilizing agent aqueous solution used in the (Preparation of porous body A), to the entire surface of the foam material B of the precursor by a gravure roller so that the hydrophilizing agent aqueous solution having a mass of 1/10 of the mass of the precursor of a porous body adheres to the precursor, and drying the precursor at 60° C. for 8 hours by using electricity. Other treatment was the same as the treatment of the (Preparation of the porous body A).

Example 3

A sanitary napkin was produced in the same manner as Example 1 except that dot printing having the number of lines (print density) of 50 lpi and a printing area ratio of 40% was used as the printing pattern of the gravure printing (water repellent finishing) for the backsheet (moisture permeable film) of Example 1, and was referred to as a sample of Example 3. Meanwhile, screentone No. 54 of Letraset (Esselte Corporation) was employed when printed dots were set.

Example 4

Figure 4:
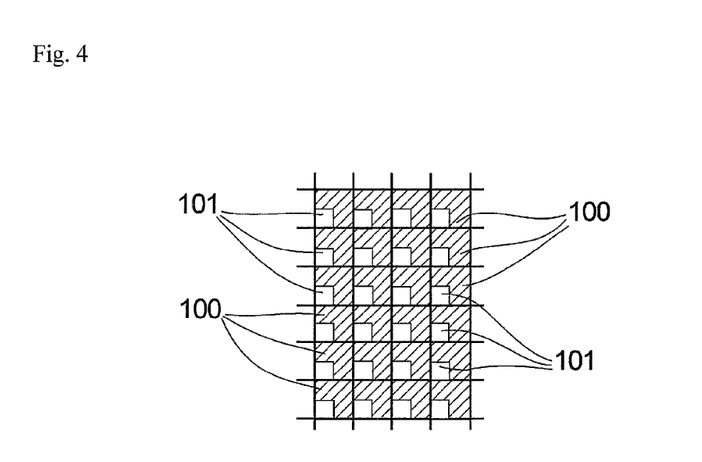
FIG. 4 is a view illustrating a printing pattern that is used in the gravure printing (water repellent finishing) for a backsheet (moisture permeable film) of Example 4.

A sanitary napkin was produced in the same manner as Example 1 except that whole surface printing, which has voids, of the printing pattern illustrated in FIG. 4 was used as the printing pattern of the gravure printing (water repellent finishing) for the backsheet (moisture permeable film) of Example 1, and was referred to as a sample of Example 4. The entire printing surface was divided into a plurality of divided regions 100 of 10 mm×10 mm as illustrated in FIG. 4 with reference to J tone "J65" (manufactured by J Corporation) as an original plate, when printed dots were set, on the basis of the printing pattern of uniform dots having the number of lines (print density) of 60 lpi and a printing area ratio of 70%, and an area of 4 mm×4 mm of one corner (a left lower corner in the embodiment illustrated in FIG. 4) of the four corners of each of the regions 100 was used as a non-printing area 101 and a plate was newly produced so that dots (hydrophobic ink) were not placed on the non-printing area 101.

Comparative Example 1

A sanitary napkin was produced in the same manner as Example 1 except that a porous body having the same structure as the porous body A except that through holes were not formed was used as the absorbent member, and was referred to as a sample of Comparative example 1.

Comparative Example 2

A sanitary napkin was produced in the same manner as Example 1 except that gravure printing (water repellent finishing) for a moisture permeable film forming a backsheet was performed not on the skin-facing surface but on the non-skin-facing surface, and was referred to as a sample of Comparative example 2.

Comparative Example 3

A sanitary napkin was produced in the same manner as Example 1 except that only the foam material A (having a basis weight of 150 g/m$^2$) was used as the absorbent member (that is, a single-layer absorbent member was used), and was referred to as a sample of Comparative example 3. Meanwhile, a hot embossing compressing process, which had the same conditions as the hot embossing used in the compression and integration of the foam materials A and B in the (Preparation of porous body A), was performed on the absorbent member made of only the foam material A.

Comparative Example 4

A sanitary napkin was produced in the same manner as Example 1 except that the absorbent member was upside down (that is, an upper layer was made of the foam material B and a lower layer was made of the foam material A), and was referred to as a sample of Comparative example 4.

Comparative Example 5

A sanitary napkin was produced in the same manner as Example 3 except that dot printing having the number of lines (print density) of 27.5 lpi and a printing area ratio of 20% was used as the printing pattern of the gravure printing (water repellent finishing) using a single-layer moisture permeable film, which had a basis weight of 20 g/m$^2$ and the moisture permeability amount (the moisture permeability amount before water repellent finishing) of 2.7 g/(100 cm$^2$·hr), and includes a plurality of microvoids as a backsheet, and was referred to as a sample of Comparative example 5. Meanwhile, screentone No. 12 of Letraset (Esselte Corporation) was employed as an original plate when printed dots were set.

Comparative Example 6

A sanitary napkin was produced in the same manner as Example 1 including the printing pattern on the backsheet except that a moisture impermeable film (a single-layer polyethylene film) having a basis weight of 20 g/m² and the moisture permeability amount (the moisture permeability amount before water repellent finishing) of 0 g/(100 cm²·hr) was used as a backsheet, and was referred to as a sample of Comparative example 6.

Comparative Example 7

A sanitary napkin was produced in the same manner as Example 1 except that dot printing having the number of lines (print density) of 60 lpi and a printing area ratio of 70% was used as the printing pattern of the gravure printing (water repellent finishing) for the backsheet (moisture permeable film) of Example 1, and was referred to as a sample of Comparative example 7. Meanwhile, a printing area ratio was adjusted to 70% by performing the expansion of each point with reference to J tone "J65" (manufactured by J Corporation) as an original plate when printed dots were set.

[Evaluation]

In regard to the samples (sanitary napkins) of Examples and Comparative examples, the Klemm water absorption height of each of the layers (upper and lower layers) of the absorbent member and the moisture permeability amount in the portion, which is located in the target region, of the backsheet were evaluated by the above-mentioned method. Further, in regard to each sample, liquid absorption time, the amount of residual liquid, the exudation property of backsheet, and the sense of use (a dry feeling, a stuffy feeling, and an exudation property of the skin-facing surface) were evaluated by the following methods, respectively. These results are illustrated in the following Tables 1 and 2.

<Liquid Absorption Time>

Each of the samples of Examples and Comparative examples was spread and placed on a laboratory table, and an acrylic liquid injection plate, which is integrally molded so that an acrylic cylindrical part having an inner diameter of 22 mm and a height of 50 mm was located above a liquid injection opening having a diameter of 10 mm, is disposed to overlap the sample so that a liquid injection hole of the liquid injection plate is located at the center of the target region of the skin-facing surface (topsheet side) of the sample, and an appropriate weight plate is placed thereon so that a load (including the weight of the liquid injection plate) is adjusted to 5 g/m². Horse defibrinated blood manufactured by Nippon Biotest Labo. is naturalized in advance at a room temperature (23° C.), and 6 g of the blood is transferred to a 100 cc liquid injection beaker. This blood is immediately injected to a tube of the liquid injection plate, and time (sec.) is measured from a moment when the injection of the blood is ended until the blood in the tube disappears so that the topsheet of the sample is exposed to the outside. Measurement is performed three times for each sample, and an average value thereof is used as the liquid absorption time of the sample. It is determined that shorter liquid absorption time means a higher liquid absorption rate. Accordingly, short liquid absorption time is evaluated highly.

<The Amount of Residual Liquid>

The liquid injection plate is immediately removed from each sample immediately after the measurement of the liquid absorption time, and each sample is left as it is for 1 minute. After that, immediately, three pieces of absorbent paper (KIMWIPE S-200 manufactured by Nippon Paper Crecia Co., Ltd.), which has been weighted in advance, and a rectangular parallelepiped weight having a width of 40 mm, a length of 70 mm, and a weight of 300 g are placed on a liquid absorption portion of the sample (a portion to which liquid is injected for the measurement of the liquid absorption time) for 30 seconds, and the amount (g) of liquid absorbed by the absorbent paper is calculated from the weight of the absorbent paper after 30 seconds. Measurement is performed three times for each sample, and an average value thereof is used as the amount of residual liquid of the sample. A value of the amount of residual liquid corresponds to the amount of horse blood remaining in the topsheet, a smaller value means a smaller amount of residual liquid and a smoother surface, and the smoother surface means a more excellent dry feeling of the skin-facing surface.

<Exudation Property of Backsheet>

A test solution is prepared and naturalized at a room temperature (23° C.). The test solution was prepared by completely mixing 30 mass % of glycerine, 0.9 mass % of sodium chloride, and about 69.1 mass % of ion-exchange water and further mixing 0.03 mass % of a food dye (blue No. 1) to color the test solution so that exudation is easily confirmed. A piece of filter paper (No. 2) having a diameter of 185 mm is disposed below each sample so that the target region is positioned at the center; 5 g of the test solution is injected using the liquid injection plate, which is used to the measurement of the liquid absorption time, under the same pressurized condition as the measurement; the plate and the weight are removed after being left as it is for 1 minute; and a weight, which has a length of 80 mm, a width of 50 mm, and a weight of 1 kg, is gently placed so as to overlap the liquid absorption surface as much as possible and is left for 1 hour. After that, the filter paper is removed, and it is checked whether a blue food dye exudes to the filter paper. Evaluation is performed five times for each sample. A case in which the number of times of exudation was 0 was determined as A, a case in which the diameter of a spot-shaped portion to which a blue food dye exuded was 5 mm or less was determined as B, and other cases were determined as C. Meanwhile, in the case of B, the number of times of exudation is shown in parentheses in Table 2.

<Sense of Use>

Sanitary napkins of Examples 1 and 2 and Comparative examples 1 to 5 were employed as samples, five female monitors who were not on their periods wore these samples together with the sanitary panties ("Laurier ACTIVE GUARD: outing mode" manufactured by Kao Corporation), and evaluated the sense of use (a dry feeling, a stuffy feeling, and a exudation property of the skin-facing surface) at that time on the basis of the following evaluation criteria. Wearing time was set to 30 minutes for each sample, and the sanitary panties having sizes appropriate for the respective monitors were prepared and were exchanged for every sample. A test solution was injected to a sample to be worn by 5 g under the same condition as the case of the exudation property of backsheet immediately before the monitor wore the sample, and the sample was provided for wearing after being left for three minutes. The test solution used here was the same as the test solution, which was used in the case of the exudation property of backsheet, except that the test solution did not use a food dye (blue No. 1) and was transparent liquid.

(Evaluation Criteria for the Sense of Use)

1. Dry Feeling of Skin-Facing Surface

After the monitor worn the sample for 30 minutes, "no stickiness" felt from the sample (sanitary napkin) was used as an index of the dry feeling of the skin-facing surface, "not sticky" was denoted by 1, "not sticky a little" is denoted by 2, "cannot say either" was denoted by 3, "sticky a little" was denoted by 4, and "sticky" was denoted by 5. The monitors were made to select numbers closest to their feelings, and an average value of the values of five monitors was obtained for each sample. A smaller average value means a drier feeling of the skin-facing surface of the sanitary napkin.

2. Stuffy Feeling

After a monitor worn the sample for 30 minutes, in regard to a stuffy feeling felt from the sample (sanitary napkin), "no stuffiness" was denoted by 1, "not stuffy a little" is denoted by 2, "cannot say either" was denoted by 3, "stuffy a little" was denoted by 4, and "stuffy" was denoted by 5. The monitors were made to select numbers closest to their feelings, and an average value of the values of five monitors was obtained for each sample. A smaller average value means less stuffiness of the sanitary napkin, and a drier feeling.

3. Exudation Property

When the sample (sanitary napkin) was removed from the sanitary panty and the monitor touch the crotch portion of the shorts with fingers after the evaluation of each of 1 and 2 was ended, each of the monitors was made to denote A when there was no wet feeling, to denote C when there was a wet feeling, and to denote B when moisture was felt a little but it was determined that there was no problem (to denote C regardless of the degree of moisture if it was determined that there was a problem). A was denoted only when the determinations of all monitors correspond to A, B was denoted if there was one B among the determinations of all monitors, and C was denoted if there was one C among the determinations of all monitors. Meanwhile, in the case of B, the number of monitors, who have felt a wet feeling, was shown in parentheses in Table 2.

TABLE 1

| | | example | | | | comparative example | |
|---|---|---|---|---|---|---|---|
| | | 1 | 2 | 3 | 4 | 1 | 2 |
| Absorbent member | Type | layer-stacked structure | layer-stacked structure | layer-stacked structure | layer-stacked structure | layer-stacked structure | layer-stacked structure |
| | Method of applying hydrophilizing agent | completely immersed | applied from lower layer | completely immersed | completely immersed | completely immersed | completely immersed |
| | Presence or absence of through hole | with through hole | with through hole | with through hole | with through hole | with no through hole | with through hole |
| | Klemm water absorption height of upper layer(mm) | 25 | 15 | 25 | 25 | 25 | 25 |
| | Klemm water absorption height of lower layer(mm) | 80 | 50 | 80 | 80 | 80 | 80 |
| | Klemm water absorption height of lower layer/ Klemm water absorption height of upper layer | 3.2 | 3.3 | 3.2 | 3.2 | 3.2 | 3.2 |
| Backsheet | Type | moisture permeable film | moisture permeable film | moisture permeable film | moisture permeable film | moisture permeable film | moisture permeable film |
| | Basis weight(g/m$^2$) | 40 | 40 | 40 | 40 | 40 | 40 |
| | Water repellent finishing (gravure printed) portion | skin-facing surface | skin-facing surface | skin-facing surface | skin-facing surface | skin-facing surface | non-skin-facing surface |
| | Ratio of total area of portions to which hydrophobic ink adheres to area of target region (%) | 50 | 50 | 40 | 55 | 50 | 50 |
| | Moisture permeability amount in portion located in target region[g/(100 cm$^2 \cdot$ hr)] | 1.4 | 1.4 | 1.6 | 1.3 | 1.4 | 1.4 |

| | | comparative example | | | | |
|---|---|---|---|---|---|---|
| | | 3 | 4 | 5 | 6 | 7 |
| Absorbent member | Type | single-layer structure | layer-stacked structure | layer-stacked structure | layer-stacked structure | layer-stacked structure |
| | Method of applying hydrophilizing agent | completely immersed | completely immersed | completely immersed | completely immersed | completely immersed |
| | Presence or absence of through hole | with through hole | with through hole | with through hole | with through hole | with through hole |
| | Klemm water absorption height of upper layer(mm) | — | 80 | 25 | 25 | 25 |
| | Klemm water absorption height of lower layer(mm) | — | 25 | 80 | 80 | 80 |
| | Klemm water absorption height of lower layer/ Klemm water absorption height of upper layer | — | 0.31 | 3.2 | 3.2 | 3.2 |
| Backsheet | Type | moisture permeable film | moisture permeable film | moisture permeable film | moisture impermeable film | moisture permeable film |
| | Basis weight(g/m$^2$) | 40 | 40 | 20 | 20 | 40 |
| | Water repellent finishing (gravure printed) portion | skin-facing surface | skin-facing surface | skin-facing surface | skin-facing surface | skin-facing surface |
| | Ratio of total area of portions to which | 50 | 50 | 20 | 50 | 70 |

TABLE 1-continued

|  | | | | | |
|---|---|---|---|---|---|
| hydrophobic ink adheres to area of target region (%) | | | | | |
| Moisture permeability amount in portion located in target region[g/(100 cm² · hr)] | 1.4 | 1.4 | 2.4 | 0 | 0.6 |

TABLE 2

| | | Example | | | | Comparative example | | | | | |
|---|---|---|---|---|---|---|---|---|---|---|---|
| | | 1 | 2 | 3 | 4 | 1 | 2 | 3 | 4 | 5 | 6 | 7 |
| Liquid absorption time (sec) | | 45 | 68 | 45 | 45 | 165 | 45 | 125 | 125 | 45 | 45 | 45 |
| Amount of residual liquid(g) | | 0.12 | 0.08 | 0.12 | 0.12 | 0.84 | 0.12 | 1.10 | 1.40 | 0.12 | 0.12 | 0.12 |
| Exudation property of backsheet | | A | A | A | A | A | B (three times) | A | A | C | A | A |
| Sense of use | Dry feeling of skin-facing surface | 1.2 | 1.4 | 1.2 | 1.2 | 4.6 | 2.0 | 4.6 | 5.0 | 1.2 | 4.6 | 3.0 |
| | Stuffy feeling | 1.2 | 1.2 | 1.2 | 1.2 | 4.0 | 2.0 | 4.2 | 4.6 | 1.2 | 4.8 | 3.0 |
| | Exudation property | A | A | A | A | A | C | A | A | C | A | A |

As apparent from the results illustrated in Tables 1 and 2, since the liquid absorption time of each Example was short (a liquid absorption rate was high) and the amount of residual liquid in each Example was small, each Example was excellent in a dry feeling of the skin-facing surface, liquid did not easily exude in each Example from the backsheet, and a good result was obtained from the evaluation of the sense of use similarly to actual use by the monitor. In contrast, mainly because through holes were not formed in the absorbent member of Comparative example 1, the liquid absorption time of Comparative example 1 was particularly long and the amount of residual liquid in Comparative example 1 was large. Accordingly, there were obtained results that a dry feeling and a stuffy feeling of the skin-facing surface were particularly inferior. Further, mainly because water repellent finishing (gravure printing using hydrophobic ink) was performed not on the skin-facing surface of the backsheet (moisture permeable film) but on the non-skin-facing surface of the backsheet in Comparative example 2, there was obtained a result that the exudation property of the backsheet was particularly inferior. Furthermore, mainly because the absorbent member of Comparative example 3 had a single-layer structure, and Comparative example 4 has larger the Klemm water absorption height in the upper layer than in the lower layer, there were obtained results that a dry feeling and a stuffy feeling of the skin-facing surface were particularly inferior similarly to Comparative example 1. Moreover, mainly because the "ratio of the total area of the portions to which the hydrophobic ink adheres (water repellent portions) to the area of the target region" (the ratio of the total area of the portions on which the water repellent finishing is performed to the area of the target region) is less than 30% in Comparative example 5, there was obtained a result that the exudation property of the backsheet was particularly inferior. Further, mainly because the ratio exceeded 60% in Comparative example 7, there were obtained results that a dry feeling and a stuffy feeling of the skin-facing surface were particularly inferior. Furthermore, since the moisture impermeable film was used as the backsheet in Comparative example 6, the moisture permeability amount in the portion of the backsheet which was located in the target region was 0. Accordingly, there were obtained results that a dry feeling and a stuffy feeling of the skin-facing surface were particularly inferior. From the above-mentioned results, in order to obtain an absorbent article (sanitary napkin) where a liquid absorption rate is high, the amount of residual liquid is small, a dry feeling of the skin-facing surface is excellent, and liquid does not easily exude from the backsheet, it is effective that 1) a specific absorbent member in which through holes are formed at a portion located at least in the target region, the absorbent member has a layer-stacked structure (two-layer structure), and the Klemm water absorption height of the lower layer is higher than that of the upper layer is used as the absorbent member, 2) a specific backsheet which is formed of a moisture permeable film and of which the skin-facing surface has been subjected to water repellent finishing (gravure printing using hydrophobic ink) is used as the backsheet.

The invention claimed is:
1. An absorbent article sanitary napkin, comprising:
a topsheet that forms a skin-facing surface;
a backsheet that forms a non-skin-facing surface;
an absorbent member that is interposed between the topsheet and the backsheet;
the sanitary napkin contains a pair of wings longitudinally extending outward from a pair of lateral side edges of the absorbent member, wherein each of the wings includes a portion of the topsheet and the backsheet; and
a target region that is disposed so as to face an excretory part of a wearer when the wearer wears the absorbent article sanitary napkin and that is located between the pair of lateral side edges of the absorbent member,
wherein the target region is a region formed between one root and the other root of the wings in the longitudinal direction,
wherein the absorbent member is a hydrophilic foam body made of a hydrophobic material subjected to hydrophilic treatment, a plurality of through holes penetrating the absorbent member in a thickness direction are formed at a portion of the absorbent member that is located in the target region, the absorbent member has a layer-stacked structure in which a plurality of layers are stacked in the thickness direction, a ratio of the Klemm water absorption height as measured according to JIS P8141, of a lower layer, which is most proximal to the backsheet, of the layer-stacked structure to that of an upper layer that is most proximal to the topsheet is 2.0 or more, the backsheet is formed of a moisture permeable film that includes a plurality of microvoids, water repellent finishing is performed on a portion, which is located in the target region, of a skin-facing surface of the moisture permeable film, so that water repellent portions are formed, and a ratio of the total area of portions on which the water repellent finishing is performed to the area of the target region is in the range of from 30% to 60%, wherein the absorbent member does not include an absorbent polymer; and wherein the upper and lower layers of the absorbent member are bonded to each other and the layers are inseparably integrated with each other.

2. The absorbent article sanitary napkin according to claim 1, wherein the water repellent finishing is performed by applying hydrophobic ink to the portion, which is located in the target region, of the skin-facing surface of the moisture permeable film by a gravure printing method, and the water repellent portions are formed of portions to which the hydrophobic ink adheres.

3. The absorbent article sanitary napkin according to claim 1, wherein the basis weight of the moisture permeable film is 18 g/m$^2$ or more, and the moisture permeability amount in the portion of the moisture permeable film located in the target region is in the range of from 1.0 g/(100 cm$^2$·hr) to 2.2 g/(100 cm$^2$·hr).

4. The absorbent article sanitary napkin according to claim 1, wherein the water repellent finishing is performed by applying hydrophobic ink to the portion, which is located in the target region, of the skin-facing surface of the moisture permeable film by a gravure printing method, the water repellent portions are formed of portions to which the hydrophobic ink adheres, the basis weight of the moisture permeable film is 18 g/m$^2$ or more, and the moisture permeability amount in the portion of the moisture permeable film located in the target region is in the range of from 1.0 g/(100 cm$^2$·hr) to 2.2 g/(100 cm$^2$·hr).

5. The absorbent article sanitary napkin according to claim 1, wherein the target region has a rectangular shape having a length of 70 mm in a longitudinal direction and a length of 30 mm in a lateral direction.

6. The absorbent article sanitary napkin according to claim 1, wherein each of the plurality of through holes has a diameter of 1 mm to 3 mm; and wherein the number of the through holes present in a unit area, which corresponds to an area of one square centimeter and has a square shape in plan view, is 3 to 8.

7. The absorbent article sanitary napkin according to claim 1, wherein the lower layer of the absorbent member faces the backsheet.

8. An absorbent article sanitary napkin, comprising:

a topsheet that forms a skin-facing surface;

a backsheet that forms a non-skin-facing surface;

an absorbent member that is interposed between the topsheet and the backsheet;

the sanitary napkin contains a pair of wings longitudinally extending outward from a pair of lateral side edges of the absorbent member, wherein each of the wings includes a portion of the topsheet and the backsheet; and a target region that is disposed so as to face an excretory part of a wearer when the wearer wears the absorbent article sanitary napkin and that is located between the pair of lateral side edges of the absorbent member, wherein the target region is a region formed between one root and the other root of the wings in the longitudinal direction, wherein the absorbent member contains a hydrophobic material subjected to hydrophilic treatment, a plurality of through holes penetrating the absorbent member in a thickness direction are formed at a portion of the absorbent member that is located in the target region, the absorbent member has a layer-stacked structure in which a plurality of layers are stacked in the thickness direction, the Klemm water absorption height as measured according to JIS P8141, of a lower layer, which is most proximal to the backsheet, of the layer-stacked structure is higher than that of an upper layer that is most proximal to the topsheet, wherein a ratio of the basis weight of the upper layer to the basis weight of the lower layer (the basis weight of the upper layer/the basis weight of the lower layer) is in the range of from 1.3 to 3, the backsheet is formed of a moisture permeable film that includes a plurality of microvoids, water repellent finishing is performed on a portion, which is located in the target region, of a skin-facing surface of the moisture permeable film, so that water repellent portions are formed, and a ratio of the total area of portions on which the water repellent finishing is performed to the area of the target region is in the range of from 30% to 60%.

* * * * *